United States Patent [19]

Sorensen

[11] 4,327,730
[45] May 4, 1982

[54] TEXTURED THERMOPLASTIC FILM AND PRODUCT MANUFACTURED THEREFROM

[75] Inventor: Eugene R. Sorensen, Springfield Township, Hamilton County, Ohio

[73] Assignee: The Proctor & Gamble Company, Cincinnati, Ohio

[21] Appl. No.: 225,944

[22] Filed: Jan. 19, 1981

Related U.S. Application Data

[63] Continuation of Ser. No. 36,253, May 4, 1979, abandoned.

[51] Int. Cl.³ .............................................. A41B 13/02
[52] U.S. Cl. .................................................. 128/287
[58] Field of Search ............................... 128/155–156, 128/284, 287, 290 R, 296

[56] References Cited

U.S. PATENT DOCUMENTS

| | | | |
|---|---|---|---|
| 3,927,673 | 12/1975 | Taylor | 128/287 |
| 3,929,135 | 12/1975 | Thompson | 128/287 |
| 3,945,386 | 3/1976 | Anczurowski et al. | 128/287 |
| 3,965,906 | 6/1976 | Karami | 128/287 |
| 3,967,623 | 7/1976 | Butterworth et al. | 128/287 |
| 4,055,180 | 10/1977 | Karami | 128/287 |

*Primary Examiner*—C. Fred Rosenbaum
*Attorney, Agent, or Firm*—John M. Pollaro; Fredrick H. Braun; Richard C. Witte

[57] ABSTRACT

A disposable diaper is disclosed having a textured topsheet of thermoplastic material. The topsheet is manufactured from a thermoplastic sheet surface of which is imparted with a multiplicity of nubbles. The nubbles do not substantially alter the macroscopic profile of the film, but do impart a more clothlike tactile impression and reduced gloss to the film.

7 Claims, 11 Drawing Figures

TEXTURED THERMOPLASTIC FILM AND PRODUCT MANUFACTURED THEREFROM

This is a continuation of application Ser. No. 36,253, filed May 4, 1979 and now abandoned.

BACKGROUND OF THE INVENTION

Disposable absorbent articles are well known in the prior art and include such articles as diapers, bandages, catamenials, and the like. Such articles generally comprise a fluid permeable topsheet overlaying an absorbent element. Many topsheet variations are taught in the prior art ranging from fibrous webs which may be woven, non-woven, or carded to perforated plastic films. The number of perforated plastic film topsheets described in the prior art alone is significant. For example, U.S. Pat. No. 3,292,619 entitled ABSORBENT DRESSING which issued to V. C. Egler on Dec. 20, 1966 and U.S. Pat. No. 3,307,545 entitled NON-ADHERENT DRESSING which issued to P. Surowitz on Mar. 7, 1967, both teach disposable absorbent bandages having perforated plastic film topsheets. In addition, U.S. Pat. No. 3,543,750 entitled PERFORATE FILM DRESSING AND METHOD OF MAKING SAME which issued to J. Meizanis on Dec. 1, 1970 and U.S. Pat. No. 3,929,135 entitled ABSORPTIVE STRUCTURE HAVING TAPERED CAPILLARIES which issued to H. Thompson on Dec. 30, 1975 likewise teach disposable absorptive structures having a perforated plastic topsheet.

As disclosed in the foregoing patents, the use of plastic film topsheets provide advantages not available with fibrous topsheets. Fibrous topsheets, however, have a clothlike feel and appearance which is aesthetically pleasing and desirable in many disposable absorbent articles such as in disposable diapers. Plastic film topsheets, on the other hand, tend to be characterized by a high degree of gloss and smoothness. These characteristics are so closely associated with plastic films that a sheet of material may be readily identified as a plastic film by its shine and texture.

Various methods have been suggested for reducing the gloss and smoothness of plastic films to give them a more clothlike appearance. U.S. Pat. No. 2,304,632 entitled WRINKLED SURFACE ARTICLE which issued to C. R. Faelten on Dec. 8, 1942 teaches molded plastic articles having irregularly rectangular shaped ridges disposed over the surface to produce what may be called a waved surface. In addition, U.S. Pat. No. 2,575,046 entitled PROCESS FOR PRODUCING ORNAMENTAL PLASTIC FILMS which issued to M. A. Chavannes et al. on Nov. 13, 1951 teaches a plastic film at least part of surface of which is undulated and exhibits a scintillating effect.

In spite of the foregoing teachings, however, the manufacturer of disposable absorbent articles heretofore had to choose between using a topsheet which provided an aesthetically pleasing clothlike appearance and a perforated plastic film topsheet which had superior performance characteristics but which exhibited a high degree of gloss and smoothness. The prior art topsheets lack the aspects of the present invention whereby a topsheet can be manufactured from a perforated plastic film having reduced gloss and smoothness.

It is therefore an object of the present invention to provide a disposable absorbent article having a perforated plastic film topsheet which exhibits a clothlike feel and appearance.

This and other objects of the invention will be readily apparent when considered in reference to the following description and when taken in connection of the accompanying drawings.

SUMMARY OF THE INVENTION

According to the present invention, an absorbent structure is manufactured having a perforated thermoplastic film topsheet overlaying an absorbent material. The topsheet is textured with a multiplicity of nubbles on at least one surface to improve the tactile impression of the thermoplastic film and to reduce its gloss. The degree of texture imparted to the topsheet may be varied by changing the size and number of the nubbles.

In addition to being textured and perforated, the topsheet may also be embossed/debossed. Embossing/debossing substantially alters the macroscopic profile of the thermoplastic film while texturing does not.

DESCRIPTION OF THE PREFERRED EMBODIMENT

Referring now to the drawings, there is shown a preferred embodiment of the present invention as it would be used in an absorbent article and, in particular, in a disposable diaper intended to be worn by an infant. It should be understood, however, that the present invention is also applicable for use in other disposable absorbent articles such as catamenial pads, bandages, incontinent pads and briefs, and the like. As used herein, the term "disposable absorbent article" refers to articles which are intended to absorb liquids such as body exudates, and further, which are intended to be discarded after a single use (i.e. they are not intended to be laundered or otherwise restored and then reused).

Figure 1:
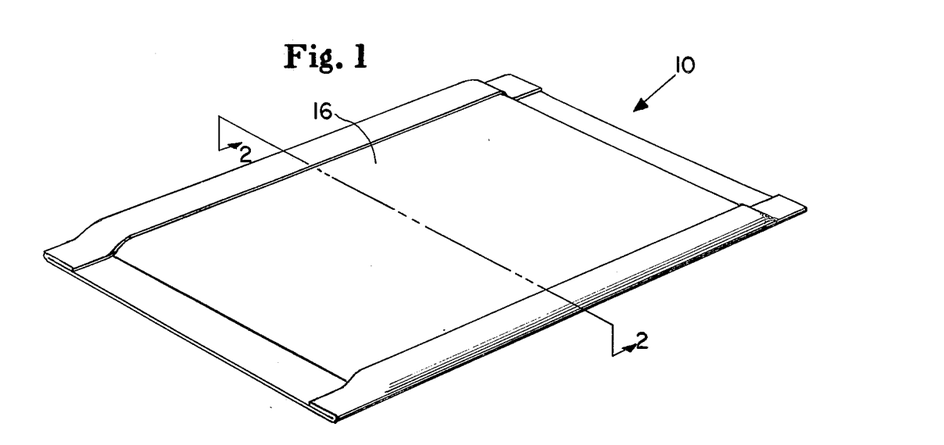
FIG. 1 is a perspective view of a disposable diaper incorporating the present invention.
Figure 2:
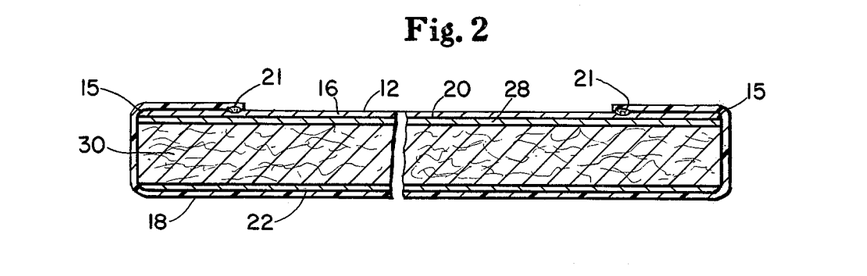
FIG. 2 is a sectional view taken along line 2—2 of FIG. 1.

FIG. 1 shows a disposable diaper 10 prior to its being applied to a diaper wearer (not shown). As best seen in FIG. 2, a preferred disposable diaper 10 comprises a fluid pervious topsheet 16, a fluid impervious backsheet 18, and an absorbent layer 30. Topsheet 16 and backsheet 18 are superposed on first and second opposed faces 20 and 22, respectively, of absorbent layer 30. Topsheet 16 may be integral with or may be affixed to backsheet 18 in any suitable manner and in any configuration as is well known in the diaper art. In the preferred embodiment, for example, backsheet 18 is folded onto and overlays longitudinal side portions 15 of topsheet 16 and is affixed thereto along longitudinal seams 21, using a suitable hot melt adhesive as is commonly used and well known in the disposable diaper art. An acceptable hot melt adhesive is sold by National Starch Company of Bridge Water, N.J. under the tradename Instant Lok 34-2933. A more detailed description of how topsheet 16, absorbent layer 30, and backsheet 18 may be assembled into a disposable diaper is given in U.S. Pat. No. Re. 26,151 entitled DISPOSABLE DIAPER which issued to Robert C. Duncan et al. on Jan. 31, 1967, said patent being incorporated herein by reference.

Impervious backsheet 18 is preferably a 0.001 to 0.002 inch (0.025 to 0.051 mm) thick polyethylene film, although other flexible, liquid impervious materials may also be used. As used herein, flexible refers to materials which are compliant and which readily conform to the shape and contours of the human body.

Still referring to FIG. 2, it can be seen that absorbent layer 30 is positioned between and encased by topsheet 16 and backsheet 18. Absorbent layer 30 may be manufactured in a wide variety of sizes and from a wide variety of absorbent materials commonly used in disposable absorbent articles capable of absorbing and retaining liquids such as absorbent foams. Other materials can also be used for absorbent layer 30 such as a multiplicity of plies of creped cellulose wadding or any equivalent material. The absorbent capacity of the material used must be sufficient to meet the expected loading in the intended use of the absorbent article. In the preferred embodiment of a disposable diaper, about 48 grams of comminuted wood pulp generally referred to as airfelt was used for absorbent layer 30.

First and second facing tissues 28 and 32, respectively, are superposed on, and are essentially coextensive with, first and second opposed faces 20 and 22, respectively, of absorbent layer 30. First and second facing tissues 28 and 32 help hold absorbent layer 30 in place and prevent lumping of absorbent layer 30. Preferred first and second facing tissues 28 and 32 have a basis weight of about 12 pounds per 3,000 sq. ft. (19 gms. per sq. meter) and an air permeability of about 100 cubic ft. per minute per sq. ft. (30.5 cubic meters per minute per sq. meter) over a 0.5 inch (12.7 mm.) water pressure drop and may be affixed to topsheet 16 and backsheet 18 as necessary to prevent shifting in use by any suitable method such as by gluing.

The size and shape of absorbent layer 30 may be varied to accommodate wearers ranging from infants to adults. The preferred embodiment illustrated in FIG. 2 is intended for infants and absorbent core 12 is therefore of a rectangular shape approximately 12½ inches (31.8 cm.) wide and 16 inches (0.6 cm.) Other shapes such as hourglass and trapezoidal configurations may also be used.

Porous topsheet 16 contacts the diaper wearer's skin and is therefore preferably compliant, soft feeling, fluid permeable, and non-irritating to the wearer's skin. More specifically, topsheet 16 is manufactured from a thermoplastic film which is perforated and which may additionally be debossed/embossed. A preferred embossed and perforated topsheet 16 is shown in U.S. Pat. No. 3,929,135 entitled ABSORPTIVE STRUCTURE HAVING TAPERED CAPILLARIES, issued to Hugh A. Thompson on Dec. 30, 1975, said patent being incorporated herein by reference. As described therein, topsheet 16 is a low density, polyethylene film having a thickness of from about 0.001 to about 0.002 inches (0.025 to 0.051 mm) although films having a thickness of less than about 0.0005 inches (0.0127 mm.) may also be used. The preferred topsheet 16 (see FIG. 3) is formed to a thickness of about 0.015 inches (0.38 mm.) with an array of tapered capillary structures 38 each having a perforated apex 34 and a base opening 36.

Figure 3:
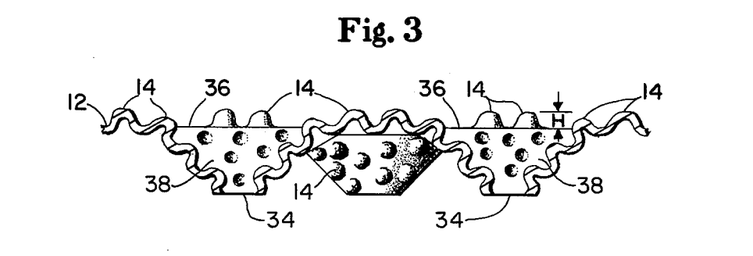
FIG. 3 is a greatly enlarged edge view representation of the topsheet of the present invention.

Still referring to FIG. 3, it can be seen that topsheet 16 has a plurality of nubbles 14 which are integral therewith and which impart an irregular and unsmooth texture to outer surface 12 of topsheet 16. For purposes of illustration, the size of nubbles 14 are greatly exaggerated. Outer surface 12 is that surface of topsheet 16 which contacts the skin of the wearer of the absorbent article (i.e., the surface not in contact with absorbent core 30). The nubbles 14 are small protuberances projecting outward from outer surface 12 and reduce the gloss of topsheet 16 and give topsheet 16 a more cloth-like tactile impression. Further, nubbles 14 do not substantially change the macroscopic profile of topsheet 16. Accordingly, topsheet 16 with nubbles 14 has a reduced plastic feel and appearance compared to thermoplastic film topsheets 16 without nubbles 14.

The number, size, and spacing of nubbles 14 may be varied within a critical range (hereinafter set forth) to give differing degrees of irregularity to outer surface 12. Nubbles 14 are preferably spherical or spheroidal in cross-section having a rounded rather than a sharp angular cross-section, although other cross sectional shapes may be used. Nubbles 14 having a cross-sectional diameter of from about 0.0005 to about 0.0110 inches (about 0.0127 to about 0.279 millimeters) have been formed in a topsheet 16 and have been found to be satisfactory in reducing the plastic feel and impression as well as the gloss of topsheet 16. Preferably, nubbles 14 have a diameter of from about 0.001 to about 0.007 inches (about 0.025 to about 0.178 millimeters) and most preferably from about 0.001 to about 0.005 inches (about 0.025 to about 0.127 millimeters). The height H of nubbles 14 is measured from outer surface 12 to the top of nubbles 14 and is at least 30% of the cross-sectional diameter.

The cross-sectional diameter of the nubbles 14 referred to hereinbefore is the average diameter of a representative number of nubbles 14 and may be determined in accordance with the following procedure. A 2 inch square (5 cm square) sample of topsheet 16 is placed under a microscope having a calibrated eye piece such as is manufactured by Baush & Lomb of Rochester, N.Y. and marketed under the tradename Stereo Zoom 7 Microscope Model No. 31-26-30-07. The diameters of nubbles 14 on the sample of topsheet 16 are visually measured and the average determined.

The same procedure as hereinbefore outlined may be used to determine the average spacing between nubbles 14. Average spacing as herein used refers to the center to center distance between individual nubbles 14. A satisfactory reduction in plastic feel and appearance is obtained when nubbles 14 have an average spacing of from about 1 to about 6 diameters. Preferably, nubbles 14 are spaced from about 2 to about 4 diameters apart and most preferably from about 2 to about 3 diameters apart.

Nubbles 14 may be formed in topsheet 16 in any of a number of ways which will suggest themselves to one skilled in the plastic film forming arts. A preferred method which was used to manufacture topsheet 16 and found to be satisfactory is disclosed in U.S. patent application Ser. No. 36,254, entitled METHOD AND APPARATUS FOR TEXTURING A THERMOPLASTIC FILM, which was filed on May 4, 1979 by Paul R. Louis et al., which application is incorporated herein by reference.

Figure 4:
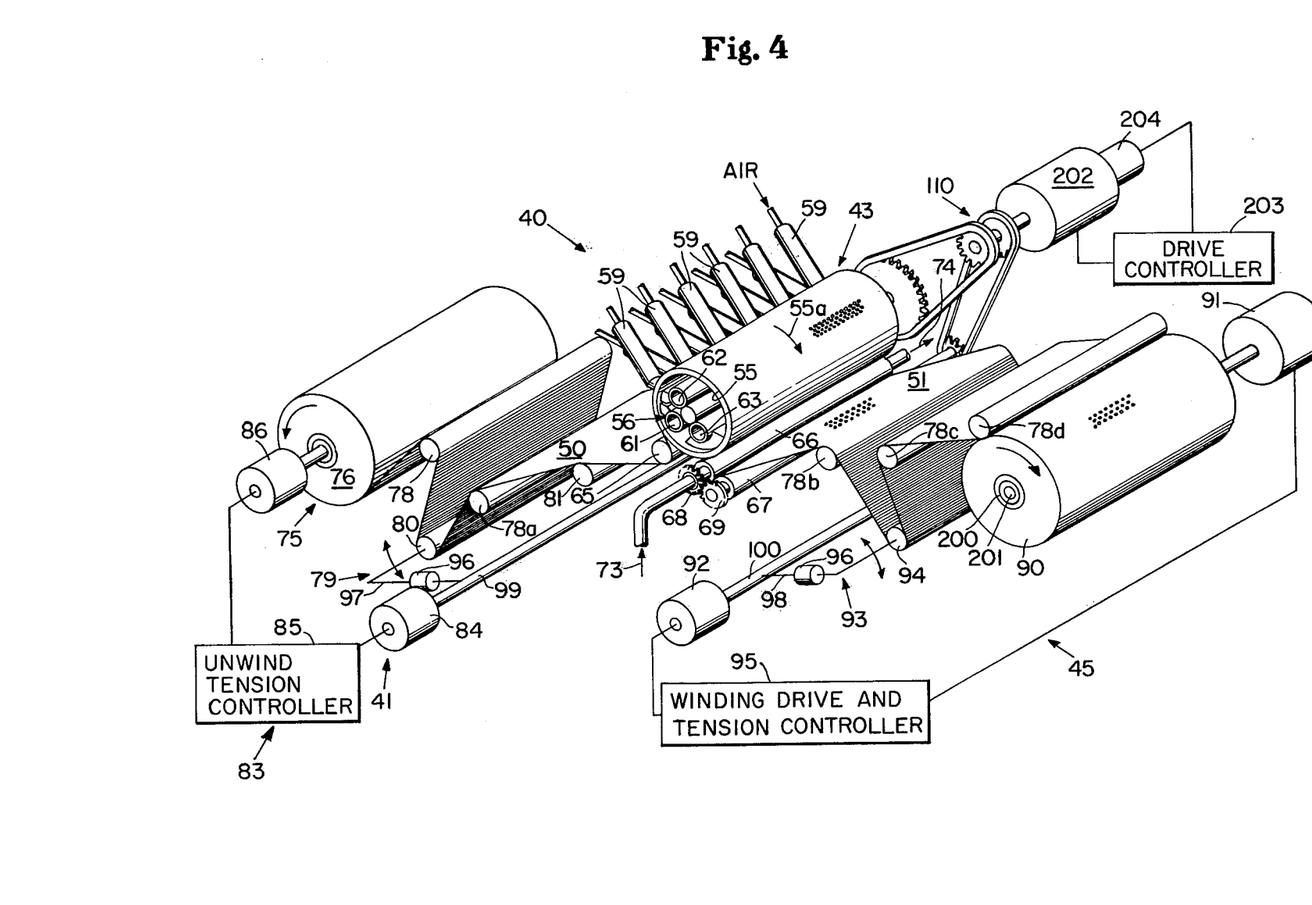
FIG. 4 is a perspective schematic view of a preferred apparatus for manufacturing the topsheet of the present invention.

A preferred apparatus 40 is shown in FIG. 4 to include constant tension film supply means 41, texturing means 43, and constant tension film forwarding and winding means 45. The frame, bearings, supports and the like which must necessarily be provided with respect to the functional members of apparatus 40 are not shown in the figures or described in detail in order to simplify and more clearly depict and disclose the present invention, it being understood that such details would be obvious to persons of ordinary skill in the art of designing thermoplastic film converting machinery. Further, except for the texturing means 43, apparatus 40 is substantially identical to the apparatus disclosed in U.S. Pat. No. 4,151,240, entitled METHOD OF AND APPARATUS FOR DEBOSSING AND PERFORATING A RUNNING RIBBON OF THERMOPLASTIC FILM which issued to M. B. Lucas et al. on Apr. 24, 1979, which patent is incorporated herein by reference.

Briefly, apparatus 40, FIG. 4 comprises means for continuously converting a ribbon of thermoplastic film 50 into a textured film 51 by directing hot air jets against one surface of the film while applying vacuum adjacent the opposite surface of the film, and while maintaining sufficient control of the film 50 to substantially obviate wrinkling and/or macroscopically distending the film. Thus, as will be more fully described hereinafter, apparatus 40 comprises means for maintaining constant machine direction tension in the film both upstream and downstream of a zone where the temperature of the film is greater than the thermoplastic temperature of the film but in which zone there is substantially zero machine-direction and transverse-machine direction tension tending to macroscopically distend the film. The tension is required to control and smooth a running ribbon of thermoplastic film; the zero tension zone results from the film in the zone being at a sufficiently high temperature to enable texturing it through the use of heat and vacuum. FIG. 4 also shows greatly enlarged scale nubbles in film 51 to enable visually perceiving the nature of the difference between the smooth film 50 and the textured film 51 as more fully described hereinafter.

Figure 5:
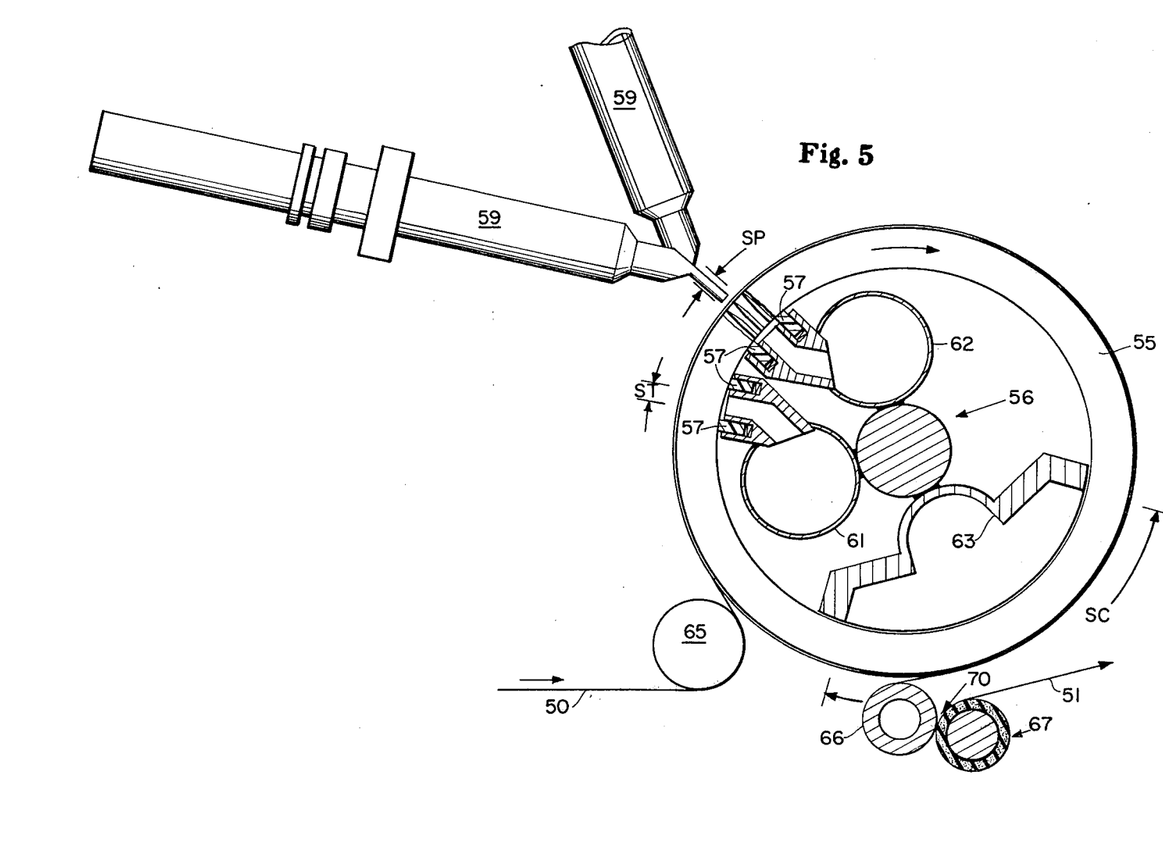
FIG. 5 is a fragmentary, enlarged scale side elevational view of the debossing/embossing and perforating cylinder portion of the apparatus shown in FIG. 4.

FIG. 5 is an enlarged scale end view of the texturing means 43, FIG. 4, which includes a rotatably mounted texturing cylinder 55, a nonrotating triplex vacuum manifold assembly 56 including seals 57, and hot air jet heaters 59. The triplex vacuum manifold assembly 56 comprises three manifolds designated 61, 62, and 63. FIG. 5 also shows a freely rotatably mounted lead-on idler roll 65, a power rotated lead-off/chill roll 66, and a soft-face (e.g., low density neoprene) roll 67 which is gear driven by the chill roll through gears 68, 69, FIG. 4. Briefly, by providing means (not shown) for independently controlling the degree of vacuum in the three vacuum manifolds, 61, 62, and 63, a thermoplastic ribbon of film running circumferentially about a portion of the texturing cylinder 55 is sequentially subjected to a first level of vacuum in a first sector ST, FIG. 5, and a second level of vacuum in a second sector SP and a third level of vacuum in a third sector SC. As will be described more fully hereinafter, the vacuum applied to the film 50 in sector ST enables maintaining upstream tension in the film 50, vacuum in sector SP urges the film 50 against the texturing cylinder 55 and enables texturing, embossing/debossing and perforating the film when hot air is directed radially inwardly against the film 50, and vacuum in sector SC enables cooling the film 51 to below its thermoplastic temperature and enables establishing downstream tension therein. The nip 70 intermediate chill roll 66 and the soft-face roll 67 is only nominally loaded because high pressure would iron-out the debossments/embossments which are alternatively designated tapered capillaries 38 (FIG. 3). However, even nominal pressure in nip 70 helps the vacuum in sector SC to isolate downstream tension (e.g., roll winding tension) from the texturing sector SP of the texturing cylinder 55, and enables the nip 70 to peel the debossed and perforated film from the texturing cylinder 55. Moreover, while vacuum drawn ambient air passing through the film in sector SC will normally cool the film to below its thermoplastic temperature, the passage of coolant through the chill roll as indicated by arrows 73, 74 in FIG. 4 will enable the apparatus to handle, for instance, thicker films, or be operated, for instance, at higher speeds.

Referring back to FIG. 4, the constant tension film supply means 41 and the constant tension film forwarding and winding means 45 are substantially identical to and function substantially identically to the corresponding portions of the apparatus shown and described in U.S. Pat. No. 3,647,221 entitled Dynamic Stress-Strain Testing of Ribbons of Film, which issued on July 4, 1972 to Coenraad E. Riemersma, which patent is hereby incorporated by reference.

Briefly, however, the constant tension film supply means 41 comprises means 75 for rotatably mounting a roll 76 of thermoplastic film, a first idler roll 78, a dancer assembly 79 having a swingably mounted freely rotatable dancer roll 80, a second idler roll 78A, a Mount Hope Vari-Bow (Registered Trademark of Mount Hope Machinery Company, Taunton, Mass. 02780) smoothing roll 81, the film-lead-on idler roll 65, and feedback film tension control means 83 comprising a dancer elevation position sensor 84, an unwind tension controller 85, and a variable-torque unwind brake 86. When the film 50 is looped from the roll 76 to the texturing cylinder 55 as shown in FIG. 4, the film 50 is urged against and adhered to the first sector ST, FIG. 5, of the texturing cylinder 55 by vacuum applied through manifold 61. Thus, the film 50 is pulled as the texturing cylinder 55 rotates clockwise as indicated by the arrow 55A, while the tension control loop causes the unwind brake 86 to sufficiently resist unwinding the roll 76 of film 50 to establish and maintain a constant predetermined level of tension in the film in the machine direction. This, in turn, enables the film 50 to be tensioned transversely as it is drawn over the Mount Hope Vari-Bow roll 81 whereby it is smoothed; i.e., made wrinkle free by having a transverse tension developed in the film as it runs over the arcuate-shaped roll 81.

The tension in the film is reduced to zero, and the film 50 is textured, debossed/embossed and perforated as it passes over the second sector SP, FIG. 5, of the rotating texturing cylinder 55. Then, the film is urged against and adhered to the third sector SC of the texturing cylinder 55 by vacuum applied to manifold 63 to enable the constant tension film forwarding and winding means 45 to again establish and maintain sufficient uniform tension in the film 51 to forward the film downstream under sufficient control to, for instance, wind the film to form a roll 90 of textured, debossed/embossed and perforated film. In this event, the torque of the winding drive motor 91 is controlled by the dancer-roll-position-responsive sensor 92 connected via trapeze 93 to dancer roll 94 through the winding drive and tension controller 95 to establish and maintain a substantially constant predetermined level of machine direction tension in film 51. To summarize, the first and third vacuum sectors, ST and SC respectively of the texturing cylinder 55 enable maintaining substantially constant upstream and downstream tension respectively in a running ribbon of film while the intermediate portion of the film adjacent the second vacuum sector SP of the texturing cylinder 55 is subjected to tension vitiating heat and vacuum to effect texturing, debossing/embossing and perforating the film.

Weights 96, FIG. 4, on the dancer trapeze arms, 97 and 98, enable independently adjusting the upstream and downstream levels of tension: higher tensions by placing the weights 96 further from the dancer shafts 99, 100; and lower tensions by moving the weights 96 towards the dancer shafts 99, 100.

Referring again to FIG. 4, the texturing means 43 comprises the rotatably mounted texturing cylinder 55, means 110 for rotating the texturing cylinder 55 at a controlled peripheral velocity, the non-rotating triplex vacuum manifold assembly 56 inside the texturing cylinder 55, means (not shown) for applying conrolled levels of vacuum inside the three vacuum manifolds 61, 62 and 63 comprising the triplex manifold assembly 56, and a plurality of air heaters 59.

Figure 6:
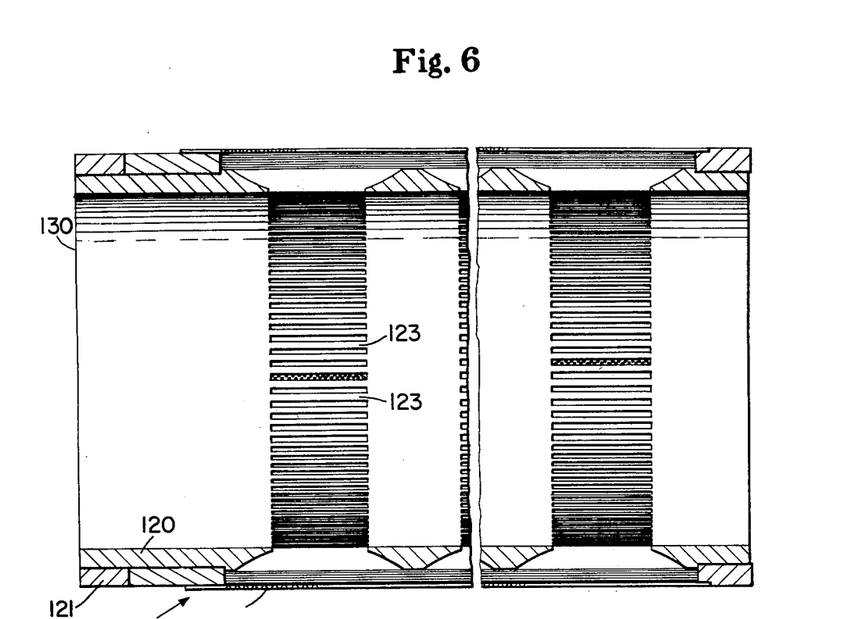
FIG. 6 is an enlarged scale, longitudinal sectional view of the debossing/embossing and perforating cylinder of the apparatus shown in FIG. 4.
Figure 7:
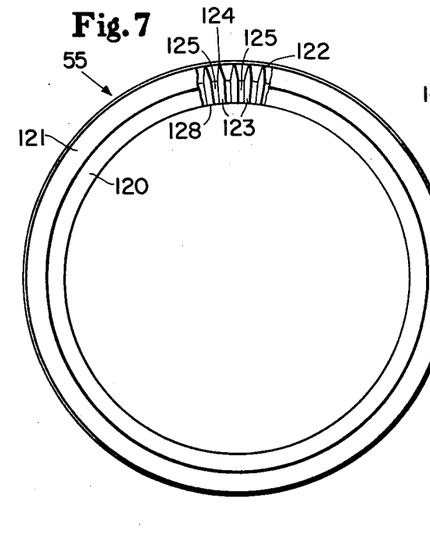
FIG. 7 is an end view of the debossing/embossing and perforating cylinder shown in FIG. 6.

The texturing cylinder 55, FIGS. 6 and 7, comprises a cage 120, a support ring 121 and a thin wall perforated tubular member 122. The cage 120 comprises a multiplicity of circumferentially spaced, longitudinally extending bars 123 which are tapered to relatively small, radially outwardly facing lands 124, and the spaced bars 123 have vacuum communicating passageways 125 provided therebetween. The bars 123 also have radially inwardly facing lands 128 which cooperately provide a cylindrical vacuum sealing surface against which the vacuum seals 57, FIG. 5, are biased. Thus, as the texturing cylinder 55 rotates, FIG. 5, its vacuum sealing surface slides over the seals 57 of the non-rotating triplex vacuum manifold assembly 56.

The end 130, FIG. 6, of the texturing cylinder 55 disposed remotely from its driven end is open in order to provide easy insertion/removal of the triplex vacuum manifold assembly 56. Therefore, in order to rotatably support the open end 130 of the texturing cylinder 55, it is provided with a bearing-race support ring 121, FIG. 6, which rides on bearings, not shown, which are appropriately secured to the apparatus frame, not shown.

Figure 8:
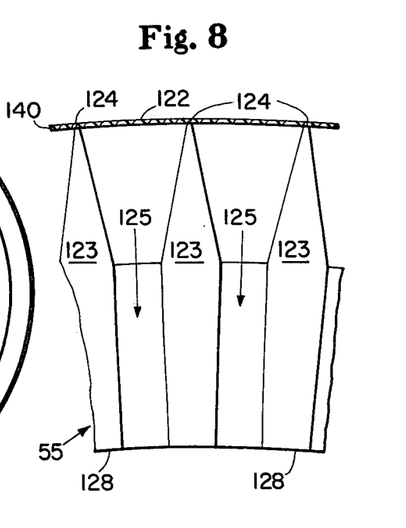
FIG. 8 is a greatly enlarged scale, fragmentary portion of the end view of the debossing/embossing and perforating cylinder shown in FIG. 6.

FIG. 8 shows the perforated tubular member 122 to comprise a thin wall 140 in contacting relation with the small lands 124 of the cage 120. The lands 124 are small and the tubular member 122 is thin-walled because the preferred embodiment apparatus 40, FIG. 4, is configured to texture, deboss/emboss and perforate a relatively thin thermoplastic film such as low density polyethylene film, thereby providing small tapered capillaries 38 as well as nubbles 14, FIG. 3.

Figure 9:
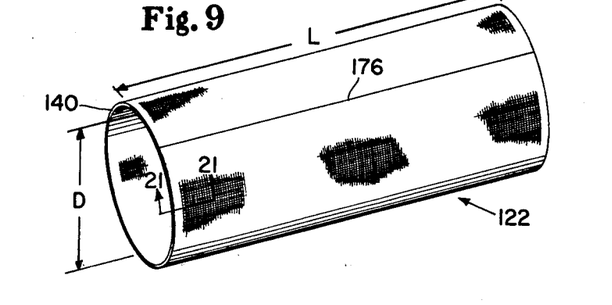
FIG. 9 is a perspective view of the perforated tubular member of the debossing/embossing and perforating cylinder shown in FIGS. 6–8, inclusive.

FIG. 9 is a perspective view of the perforated tubular member 122 of the texturing cylinder 55 having a diameter D and length L. In the preferred embodiment, D is 8.914 inches (22.64 centimeters) and L is 21.50 inches (54.61 centimeters). Also, the member has a longitudinally extending seam, 176.

Figure 10:
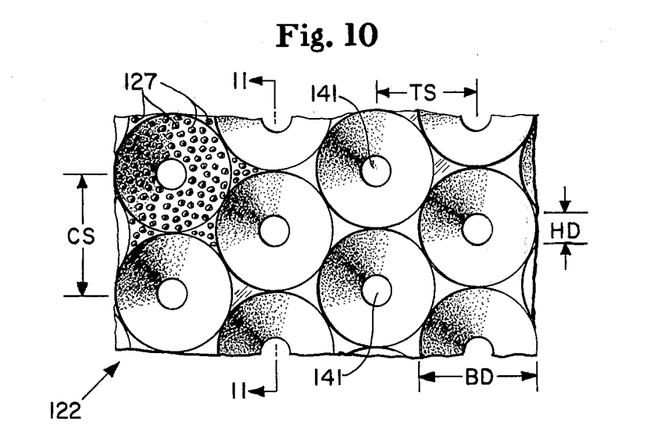
FIG. 10 is an enlarged scale, fragmentary view of the radially outwardly facing surface of the perforated tubular member shown in FIG. 9.
Figure 11:
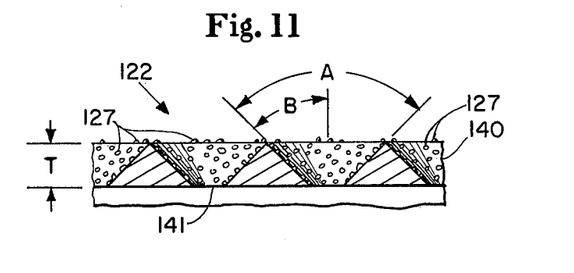
FIG. 11 is an enlarged scale fragmentary sectional view taken along line 11—11 of FIG. 10.

FIG. 10 is a radially inwardly facing, enlarged scale view of a fragmentary portion of the perforated tubular member 122. FIG. 11 is a further enlarged scale sectional view taken along line 11—11 of FIG. 10. Thus, the perforated tubular member 122 of the preferred embodiment apparatus 40 comprises a thin wall 140 having a thickness T (from about 0.013 inches to about 0.014 inches), and having a closely packed array of tapered holes 141 therethrough. The holes 141, FIG. 10, are circumferentially spaced (CS) 0.040 inches (0.102 centimeters) center-to-center, transversely spaced (TS) 0.0346 inches (0.088 centimeters) center-to-center, have base diameters (BD) of 0.040 inches (0.102 centimeters), and hole diameters (HD) of 0.013-0.014 inches (0.0330 to 0.0356 centimeters). The holes 141, FIG. 11, have included angles A of 90 degrees, and included half angles B of 45 degrees. Thus, the perforated tubular member 122 of the preferred embodiment apparatus 40 has approximately four-hundred-thirty-five-thousand (435,000) holes 141 in it.

Still referring to FIGS. 10 and 11, it can be seen that particles 127 are affixed to tubular member 122 in any suitable manner. For purposes of illustration, the size of particles 127 is greatly enlarged. In a preferred method, tubular member 122 is cleaned thoroughly with methyl ethyl keytone or vapor degreasing techniques in order to totally expose the base metal of tubular member 122. The cleaned tubular member 122 is coated with a mixture of particles 127 and epoxy which may be electrostatically sprayed onto tubular member 122 using any suitable spraying system such as is manufactured by Metokote Equipment Company of Lima, Ohio and marketed under the tradename Meco 10. Aluminum oxide particles were used and found to be satisfactory. After spraying the mixture of aluminum oxide particles and epoxy onto tubular member 122, the epoxy is cured.

By varying the ratio of particles 127 to epoxy, the texture of the film 51 is varied. Similarly, varying the size of particles 127 (as measured by the average particle diameter) will also vary the texture of film 51. Table I sets forth some of the aluminum oxide particle sizes and ratios of aluminum oxide particles to epoxy which were used and found to be satisfactory.

TABLE I

| Average Particle diameter (inches) | 0.0025 | 0.00225 | 0.00195 | 0.0016 |
|---|---|---|---|---|
| Ratio of particles to epoxy (by wt.) | 2.3:1 | 3:2 | 3:2 | 1.1:1 |

An acceptable epoxy is manufactured by Armstrong Products Company of Warsaw, Ind. and marketed under the tradename Armstrong Vibro-Flo E-7000 Series. Suitable aluminum oxide particles 127 are manufactured by General Abrasives Company of Niagara Falls, N.Y. and are marketed under the tradename Lionblast. The aluminum oxide particles should be sorted by size which may be conveniently done by passing the particles 127 through a series of U.S. standard sieves such as those manufactured by W. S. Tyler Company of Cleveland, Ohio. Those particles which were found to work well had a diameter of from about 0.0015 to about 0.0030 inches (about 0.038 to about 0.076 mm.) and were found to produce nubbles 14 of the diameter within the ranges hereinbefore stated when the topsheet 16 thickness used was 0.001 inches (0.025 mm.).

Heaters 59 of the preferred apparatus, FIGS. 1 and 4, are Model No. 33-HS which are available from Kamweld Products Company, Inc., 90 Access Rd., P.O. Box 91, Norwood, Mass. 02062. When operated on 120 volts, they provide 900 watts of heat and cause a flow of 6–8 cfm to be heated approximately 243° C.; substantially higher than the thermoplastic temperature of low density polyethylene.

The method of making perforated tubular member 122 is described in detail in the aforementioned U.S. patent application Ser. No. 733,961.

To operate apparatus 40, the film 50 is looped, as shown in FIG. 4, from roll 76, over idler roll 78, under dancer roll 80, over idler roll 78A, over the Mount Hope Vari-Bow roll 81, under the lead-on idler roll 65, clockwise about the texturing cylinder 55, under the lead-off/chill roll 66, through the nip 70 intermediate the lead-off chill roll 66 and the soft-face roll 67, over idler roll 78B, under dancer roll 94, over idler roll 78C, and thence onto a spool 200 on the roll winding shaft 201. The idler roll 78D is mounted so that it is gravitationally loaded against the top portion of the roll 90 being wound. The unwind tension control loop and the winding tension control loop are activated. The drive motor 202 is then operated by the drive controller 203 in response to operator inputs and in response to the feedback tachometer 204 to rotate the texturing cylinder 55 at a predetermined peripheral speed, and the chill roll 66 at a slightly higher (slack obviating) peripheral speed. The tension control loops respond to establish and maintain their respective predetermined levels of tension (as determined by the positions of weights 96) substantially irrespective of the film velocity.

Air is then directed through heaters 59, FIG. 4, and electrical power is applied thereto whereby jets of hot air issue from the heaters 59 to form a virtual curtain of hot air directed radially inwardly towards sector SP, FIG. 5, of the texturing cylinder 55. With sufficient levels of vacuum applied to sectors ST and SC to isolate sector SP from upstream and downstream tension, vacuum applied to sector SP acts in concert with the hot air jets to texture, deboss/emboss and perforate the film.

When the preferred apparatus is used to texture, deboss/emboss and perforate low density polyethylene having a thickness of 0.001 inches at 50 feet per minute, the upstream tension is adjusted to about 8 ounces per lineal inch, the downstream tension is adjusted to about 2 ounces per lineal inch, and the levels of vacuum applied to sectors ST, SP, and SC are 5, 15, and 5 inches of mercury respectively.

While the preferred embodiment apparatus has been shown and described as comprising unwinding and winding means, these limitations are not believed to be critical to the present invention. Indeed, while these and other aspects have been illustrated and described, it will be obvious to those skilled in the art that various changes and modifications can be made.

What we claim is:

1. A disposable diaper comprising: a fluid permeable topsheet, said topsheet being a thermoplastic film having a plurality of perforations and a plurality of nubbles, said nubbles having a diameter of from about 0.0005 to about 0.011 inches; said nubbles being interposed between said perforations a fluid impermeable backsheet affixed to said topsheet; an absorbent means for absorbing liquids, said absorbent means being encased by said topsheet and said backsheet.

2. A disposable absorbent structure comprising: a fluid permeable topsheet, said topsheet being a thermoplastic film having a plurality of perforations and a plurality of nubbles, said nubbles having a diameter of from about 0.0005 to about 0.011 inches; said nubbles being interposed between said perforations a fluid impermeable backsheet affixed to said topsheet; an absorbent means for absorbing liquids, said absorbent means being encased by said topsheet and said backsheet.

3. The disposable diaper of claim 1 or 2, wherein said nubbles have a diameter of from about 0.001 to about 0.007 inches.

4. The disposable diaper of claim 1 or 2, wherein said nubbles have a diameter of from about 0.001 to about 0.005 inches.

5. The disposable diaper of claim 1 or 2, wherein said nubbles have an average spacing of from about 1 to about 6 diameters.

6. The disposable diaper of claim 1 or 2, wherein said nubbles have an average spacing of from about 2 to about 4 diameters.

7. The disposable diaper of claim 1 or 2, wherein said nubbles have an average spacing of from 2 to about 3 diameters.

* * * * *

UNITED STATES PATENT AND TRADEMARK OFFICE
CERTIFICATE OF CORRECTION

PATENT NO. : 4,327,730
DATED : May 4, 1982
INVENTOR(S) : Eugene R. Sorensen

It is certified that error appears in the above-identified patent and that said Letters Patent are hereby corrected as shown below:

Column 3, line 63, "0.6cm" should read --40.6cm--.

Column 4, line 60, "Stereo" should read --Stero--.

Signed and Sealed this

Twenty-fifth Day of June 1985

[SEAL]

Attest:

DONALD J. QUIGG

Attesting Officer     Acting Commissioner of Patents and Trademarks